United States Patent [19]

Hoelderich et al.

[11] Patent Number: 4,943,667
[45] Date of Patent: Jul. 24, 1990

[54] PREPARATION OF PHENYLETHANOLS

[75] Inventors: Wolfgang Hoelderich, Frankenthal; Norbert Goetz, Worms; Leopold Hupfer, Friedelsheim, all of Fed. Rep. of Germany

[73] Assignee: BASF Aktiengesellschaft, Ludwigshafen, Fed. Rep. of Germany

[21] Appl. No.: 296,766

[22] Filed: Jan. 13, 1989

[30] Foreign Application Priority Data

Jan. 16, 1988 [DE] Fed. Rep. of Germany ....... 3801106

[51] Int. Cl.$^5$ ..................... C07C 29/15; C07C 29/132
[52] U.S. Cl. ................................ 568/814; 568/815; 568/715; 568/881
[58] Field of Search ................ 568/715, 814, 815, 881

[56] References Cited

U.S. PATENT DOCUMENTS

| | | |
|---|---|---|
| 4,064,186 | 12/1977 | Gibson et al. |
| 4,495,371 | 1/1985 | Neri et al. ............. 568/427 |
| 4,512,961 | 4/1985 | Scherzer et al. ...... 423/328 |
| 4,546,208 | 10/1985 | Weiger et al. ........ 568/814 |

FOREIGN PATENT DOCUMENTS

| | | | |
|---|---|---|---|
| 531444 | 1/1956 | Canada ................ 568/881 |
| 3239611 | 5/1983 | Fed. Rep. of Germany ...... 568/814 |
| 1151145 | 7/1986 | Japan ................... 568/427 |
| 1055734 | 11/1983 | U.S.S.R. .............. 568/814 |
| 678589 | 9/1952 | United Kingdom ....... 568/814 |
| 760768 | 11/1956 | United Kingdom ....... 568/814 |

Primary Examiner—Werren B. Lone
Attorney, Agent, or Firm—Keil & Weinkauf

[57] ABSTRACT

Phenylethanols of the formula

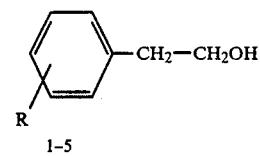

where R is hydrogen, alkyl of from 1 to 4 carbon atoms, alkoxy of from 1 to 4 carbon atoms, fluorine, trifluoromethyl or trifluoromethoxy, are prepared by reacting epoxides of the formula

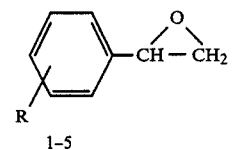

where R is as defined above, in the presence of hydrogen over zeolites and/or phosphates, doped with hydrogenating metal as catalysts, preferably over zeolites of the pentasil type.

8 Claims, No Drawings

PREPARATION OF PHENYLETHANOLS

The present invention relates to a process for preparing phenylethanols by reacting styrene oxides with hydrogen in the presence of zeolites and/or phosphates doped with hydrogenating metals.

Phenylethanols are important scents which are widely used in the perfumery and cosmetics industry. In industry, phenylethanol is prepared from benzene and ethylene oxide in the presence of a Lewis catalyst such as $AlCl_3$. This disadvantageously gives rise to problems with corrosion, catalyst removal and waste water pollution. Also, the yield is still worthy of improvement.

It is also known that phenylethanols are obtained on hydrogenating styrene oxides with Raney Ni or Pd on activated carbon in a basic medium (DE No. 2,641,821) or over a Raney Co Pd catalyst (JP No. 77/108,940) or over rhodium complexes (J. Org. Chem. 46 (1981), 2287-2290) or with diborane together with $H_2O_2$ (Aust. J. Chem. 30 (1977), 141-150). Here the disadvantage is the need to remove the suspension catalyst or homogeneous catalyst or the use of readily flammable reagents.

DE Pat. No. 2,206,805 describes the conversion of styrene oxide into phenylethanol at from 20° to 120° C. over a Pd catalyst on an $SiO_2$ or $Al_2O_3$ carrier. The disadvantage is that the reaction must be carried out in an organic solvent such as n-hexane and under high pressures of from 100 to 300 atm.

The disadvantages of existing processes for preparing phenylethanols from styrene oxides are so serious that this pathway has not been able to compete in industry with the production from benzene and ethylene oxide.

We have found that phenylethanols of the formula

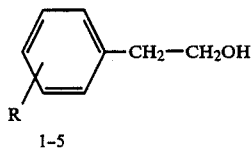

(I)

where R is hydrogen, alkyl of from 1 to 4 carbon atoms, alkoxy of from 1 to 4 carbon atoms, fluorine, trifluoromethyl or trifluoromethoxy, are obtained on reacting epoxides of the formula (II)

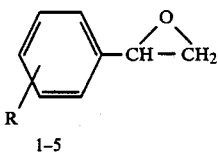

(II)

where R is as defined above, in the presence of hydrogen over zeolites and/or phosphates doped with hydrogenating metals as catalysts.

With the process according to the invention, the aforementioned disadvantages of existing processes are avoided and the catalyst requirements concerning high selectivity are met together with high conversion, long lifetime and good regenerability. Further advantages of the process according to the invention are: complete conversion, no separating problems, long times on stream, high selectivities, even for fluorine-containing compounds, simple isolation of the end products, and easy regenerability of the catalysts in the event of coking.

The starting materials used can be for example styrene oxide, p-fluorostyrene oxide, 2,4-difluorostyrene oxide, 3,4-difluorostyrene oxide, 2,4,5-trifluorostyrene oxide, o-, m- or p-trifluoromethylstyrene oxide, o-, m-or p-methylstyrene oxide, o-, m- or p-methoxystyrene oxide, 2,3,4,5-tetrafluorostyrene oxide, p-trifluoromethoxystyrene oxide, 2-fluoro-4-trifluoromethylstyrene oxide, 2-fluoro-4-trifluoromethoxystyrene oxide and 2-methyl-4-fluorostyrene oxide.

The catalysts used for the process according to the invention are acidic zeolitic catalysts. Zeolites are crystalline aluminosilicates which have a highly ordered structure comprising a rigid three-dimensional network of $SiO_4$ and $AlO_4$ tetrahedra linked by common oxygen atoms. The ratio of the Si and Al atoms:oxygen is 1:2 (see Ullmann's Encyclopädie der technischen Chemie, 4th edition, volume 24, page 575 (1983)). The electrovalence of the aluminum-containing tetrahedra is balanced by the inclusion of cations, for example an alkali metal or hydrogen ion, in the crystal. Cation exchange is possible. The spaces between the tetrahedra are occupied by water molecules prior to dehydration through drying or calcination.

In zeolites, the aluminum in the lattice may also be replaced by other elements, such as B, Ga, Fe, Cr, V, As, Sb, Bi or Be, or mixtures thereof, or the silicon may be replaced by a tetravalent element such as Ge, Ti, Zr or Hf.

Catalysts particularly suitable for the process according to the invention are zeolites of the mordenite group or narrow-pored zeolites of the erionite or chabazite type or zeolites of the faujasite type, for example Y-, X- or L-zeolites. This group of zeolites also includes the ultrastable zeolites of the faujasite type, i.e. dealuminized zeolites. Methods for preparing such zeolites are described in Catalysis by Zeolites volume 5 of Studies in Surface Science and Catalysis ed. B. Imelik et al. Elsevier Scientific Publishing Comp., 1980, page 203, and Crystal Structures of Ultra-stable Faujasites, Advances in Chemistry Series No. 101, American Chemical Society Washington DC, pages 226 ff (1971), and in U.S. Pat. No. 4,512,961.

It is particularly advantageous to use zeolites of the pentasil type. Their common basic building block is a pentagon composed of $SiO_4$ tetrahedra. They are characterized by a high $SiO_2/Al_2O_3$ ratio and by pore sizes between those of zeolites of type A and those of type X or Y (cf. Ullmann's as cited).

These zeolites can have different chemical compositions. They can be aluminosilicate, borosilicate or iron, beryllium, gallium, chromium, arsenic, antimony or bismuth silicate zeolites or mixtures thereof and aluminogermanate, borogermanate and gallium or iron germanate zeolites or mixtures thereof. Particularly suitable for the process according to the invention are the aluminosilicate, borosilicate and iron silicate zeolites of the pentasil type. The aluminosilicate zeolite is prepared for example from an aluminum compound, preferably $Al(OH)_3$ or $Al_2(SO_4)_3$, and a silicon component, preferably finely divided silicon dioxide, in an aqueous amine solution, in particular in polyamines such as 1,6-hexanediamine or 1,3-propanediamine or triethylenetetramine solution, in the presence or in particular in the absence of alkali or alkaline earth metal at from 100° to 220° C. under autogenous pressure. This also includes the isotactic zeolites described in EP No. 34,727 and EP No. 46,504. The aluminosilicate zeolites obtained have an $SiO_2/Al_2O_3$ ratio of from 10 to 40,000, depending on the mixing ratio of the starting materials. Such aluminosilicate zeolites can also be synthesized in an ether medium such as diethylene glycol dimethyl ether, in an alcohol medium such as methanol or 1,4-butanediol, or in water.

Borosilicate zeolite is synthesized under autogenous pressure, for example at from 90° to 200° C., by reacting a boron compound, for example $H_3BO_3$, with a silicon compound, preferably finely divided silicon dioxide, in an aqueous amine solution, in particular in 1,6-hexanediamine, 1,3-propanediamine or triethylene tetramine solution, in the presence or in particular in the absence of alkali or alkaline earth metal. They also include the isotactic zeolites described in EP No. 34,727 and EP No. 46,504. These borosilicate zeolites can also be prepared by carrying out the reaction not in an aqueous amine solution but alternatively in an ether solution, for example diethylene glycol dimethyl ether, or in an alcohol solution, for example 1,6-hexanediol.

Iron silicate zeolites are obtained for example from an iron compound, preferably $Fe_2(SO_4)_3$, and a silicon compound, preferably finely divided silicon dioxide, in an aqueous amine solution, in particular 1,6-hexanediamine, in the presence or absence of alkali or alkaline earth metal at from 100° to 200° C. under autogenous pressure.

The usable high-silicon zeolites ($SiO_2/Al_2O_3 \leq 10$) also include the various ZSM types, ferrierite, NU-1 and Silicalit ®, a silica polymorph molecular sieve.

The aluminosilicate, borosilicate and iron silicate zeolites thus prepared, after they have been isolated, dried at from 100° to 160° C., preferably at 110° C., and calcined at from 450° to 550° C., preferably at 500° C., can be combined with a binder in a ratio of from 90:10 to 40:60 % by weight and molded into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$, and clay. After molding, the extrudates or tablets are dried at 110° C./16 h and calcined at 500° C./16 h.

It is also possible to obtain advantageous catalysts by molding the isolated aluminosilicate or borosilicate zeolite immediately after drying and subjecting it to calcination only after the molding. The aluminosilicate and borosilicate zeolites prepared can be used in the pure form, without binder, as extrudates or tablets, the extrusion or peptization aids used being for example ethylcellulose, stearic acid, potato starch, formic acid, oxalic acid, acetic acid, nitric acid, ammonia, amines, silicoesters and graphite or mixtures thereof.

If the zeolite, on account of its manner of preparation, is present not in the catalytically active, acidic H-form but, for example, in the Na-form, it can be completely or partially converted into the desired H-form by ion exchange, for example with ammonium ions and subsequent calcination, or by treatment with acids.

Suitable hydrogenating components for inclusion in the molded or unmolded zeolites are transition metals such as metals of group VIII, such as Fe, Co, Ni, Ru, Rh, Pd, Os, Ir or Pt, and of subgroups 1 and 2, such as Cu, Ag, Zn or mixtures thereof. This doping can also be effected by ion exchange or by impregnation with metal salts.

Advantageously, doping is carried out in a riser tube by introducing the molded zeolite initially and passing an aqueous or ammoniacal solution of a halide or nitrate of the above-described metals over it at from 20° to 100° C. Such an ion exchange can take place with the hydrogen, ammonium or alkali metal form of the zeolite. Another way of applying metal to the zeolite comprises impregnating the zeolitic material with, for example, a halide, nitrate or oxide of the metal in aqueous, alcoholic or ammoniacal solution. Both ion exchange and impregnation are followed by at least one drying step, optionally by another calcination.

A possible embodiment comprises for example dissolving $Cu(NO_3)_2 \times 3$ $H_2O$ or $Ni(NO_3)_2 \times 6$ $H_2O$ or $Pd(NO_3)_2$ in water and impregnating the molded or unmolded zeolite with this solution for a certain period, for example 30 minutes. Any supernatant solution is stripped of water in a rotary evaporator. The impregnated zeolite is then dried at about 150° C. and calcined at about 550° C. This impregnating step can be carried out repeatedly in succession until the desired metal content is obtained.

It is also possible to prepare an aqueous $Ni(NO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and passing an aqueous $Ni(NO_3)_2$ solution or ammoniacal $Pd(NO_3)_2$ solution over it in a recycle loop at slightly elevated temperatures of from 30° to 80° C. for from 15 to 20 hours. This is followed by washing out with water, drying at about 150° C. and calcination at about 550° C. With some metal-doped zeolites, for example Pd-, Cu- or Ni- doped zeolites, an aftertreatment with hydrogen is advantageous.

In some cases it is advantageous to reduce the catalyst before the start of the reaction. For example, a Pt-, Pd- or Cu-doped zeolite catalyst is heated in a reactor to from 170° to 220° C. under $N_2$, and $H_2$ is then slowly added. The temperature is kept constant until no further $H_2O$ escapes.

By impregnation and ion exchange it is possible to apply multiple metals as hydrogenating components at the same time.

When the zeolitic catalysts become deactivated due to coking in the course of the reaction, it is advisable to regenerate the zeolites by burning off the coke deposit with air or with an air/$N_2$ mixture at from 400° to 550° C., preferably 500° C. This restores the zeolites to their initial activity level.

By partial precoking it is possible to set the activity of the catalyst for optimum selectivity in respect of the desired reaction product. To influence the activity and selectivity in a specific manner it is also possible to carry out a pretreatment, for example with $H_2S$ or a sulfur-containing organic compound, for example mercaptans or thiourea, at from 150° to 300° C. or a sulfur-containing inorganic compound, for example dithionite or ammonium sulfide or polysulfide. The sulfur treatment can take place for example by impregnation or by passing a sulfur-containing gas over the catalyst.

To obtain a very high selectivity, high conversions and long times on stream, it may be advantageous to modify the zeolites. A suitable method of modifying the catalysts comprises for example doping, in addition to the above hydrogenating components, the molded or unmolded zeolite with metal salts by ion exchange or impregnation. The metals used are alkali metals such as Li, Cs or K, alkaline earth metals such as Mg, Ca, Sr, or Ba, metals of main groups III, IV and V, such as B, Al, Ga, Ge, Sn, Pb or Bi, and rare earth metals such as La, Ce, Pr, Nd, Er, Yb or U. The modification with these metals can be effected simultaneously with the application of the hydrogenating component by ion exchange or impregnation or follow the application of the hydrogenating component and possibly a subsequent calcination.

Advantageously, doping is carried out by introducing for example the molded zeolite into a riser pipe and passing for example an aqueous or ammoniacal solution of a halide or nitrate of one of the abovementioned metals over it at from 20° to 100° C. Such an ion exchange can take place, for example, with the hydrogen, ammonium, or alkali metal form of the zeolite. Another way of applying metal to the zeolite comprises impregnating the zeolitic material with, for example, a halide, nitrate or oxide of one of the abovementioned metals in aqueous, alcoholic or ammoniacal solution. Both ion exchange and impregnation are followed by at least one drying step, optionally by another calcination.

A possible embodiment comprises for example dissolving $Ce(NO_3)_3 \times 6\ H_2O$ or a $(NO_3)_2 6\ H_2O$ or $Cs_2CO_3$ or $H_2WO_3$ in water and impregnating the molded or unmolded zeolite with this solution for a certain period, for about 30 minutes. Any supernatant solution is stripped of water in a rotary evaporator. The impregnated zeolite is then dried at about 150° C. and calcined at about 550° C. This impregnating step can be carried out repeatedly in succession until the desired metal content is obtained.

It is also possible to prepare, for example, an aqueous $Ce(NO_3)_3$ solution or $Mg(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and for example passing an aqueous $Ce(NO_3)_2$ solution or $Mg(NO_3)_2$ solution over it in a recycle loop at slightly elevated temperatures of from 30° to 80° C. for from 15 to 20 hours. This is followed by washing out with water, drying at about 150° C. and calcination at about 550° C.

A further method of modifying the zeolite comprises treating the zeolitic material, which may be in molded or unmolded form, with an acid such as hydrochloric acid, hydrofluoric acid or phosphoric acid and/or steam. This type of modification may be followed by application of the hydrogenating component, advantageously, for example, by treating the zeolite in pulverulent form with 1N phosphoric acid at 80° C. for 1 hour and then washing with water and drying at 110° C./16 h and calcining at 500° C./20 h. Alternatively, before or after being molded together with a binder, the zeolite is treated at from 60° to 80° C. with from 3 to 25% strength by weight, in particular from 12 to 20% strength by weight aqueous hydrochloric acid for example for from 1 to 3 hours. Afterwards, the zeolite thus treated is washed with water, dried and calcined at from 400° C. to 500° C. This is followed by the application of the hydrogenating component by ion exchange or impregnation as described.

In a particular embodiment, the acid treatment comprises treating the zeolitic material, before it is molded, with 0.001N to 2N, preferably 0.05N to 0.5N, hydrofluoric acid at elevated temperatures, for example, by refluxing for in general from 0.5 to 5, preferably from 1 to 3, hours. After the zeolitic material has been isolated by filtering and washing, it is advantageously dried, at from. 100° to 160° C. and calcined at from 450° C. to 600° C. In a further preferred embodiment, the zeolitic material, after it has been molded together with a binder, is treated at elevated temperatures, advantageously at from 50° to 90° C., preferably at from 60 to 80° C., for from 0.5 to 5 hours with, preferably, from 12 to 20% strength by weight hydrochloric acid. The zeolitic material is subsequently washed and expediently dried at from 100° to 160° C. and calcined at from 450° to 600° C. An HF treatment can also be followed by an HCl treatment. This is followed by the application of the hydrogenating component as described.

In another procedure, zeolites can be modified by applying phosphorus compounds, such as trimethoxyphosphate, trimethoxyphosphine or primary, secondary or tertiary sodium phosphate. To this end, the zeolites are impregnated in extruded, tablet or fluidizable form with for example aqueous phosphate solution, dried at 110° C. and calcined at 500° C. Then the hydrogenating component is applied as described above.

Further catalysts for the process according to the invention are phosphates, in particular aluminum phosphates, silicon aluminum phosphates, silicon iron aluminum phosphates, cobalt aluminum phosphate, cobalt silicon aluminum phosphate, cerium phosphate, zirconium phosphates, boron phosphate, iron phosphate, strontium phosphate or mixtures thereof.

The aluminum phosphate catalysts used for the process according to the invention are in particular those aluminum phosphates which have been synthesized under hydrothermal conditions. Suitable aluminum phosphates are for example APO-5, APO-9, APO-11, APO-12, APO-14, APO-21, APO-25, APO-31 and APO-33. For instance, $AlPO_4$-5 (APO-5) is synthesized by preparing a homogeneous mixture of orthophosphoric acid with pseudoboehmite (Catapal SB®) in water, adding tetra-propylammonium hydroxide to this mixture and then heating at about 150° C. under autogenous pressure in an autoclave for from 20 to 60 hours. The $AlPO_4$ is filtered off, dried at from 100° to 160° C. and calcined at from 450° to 550° C.

$AlPO_4$-9 (APO-9) is likewise synthesized from orthophosphoric acid and pseudoboehmite but in an aqueous DABCO solution (1,4-diazabicyclo[2.2.2]octane) at about 200° C. under autogenous pressure in the course of from 200 to 400 hours. If ethylenediamine is used instead of DABCO, APO-12 is obtained.

AlPO-21 (APO-21) is synthesized from orthophosphoric acid and pseudoboehmite in an aqueous pyrrolidone solution at from 150° to 200° C. under autogenous pressure in the course of from 50 to 200 hours.

Silicon aluminum phosphates, e.g. SAPO-5, SAPO-11, SAPO-31 and SAPO-34 may also be used in the process. These compounds are prepared by crystallization from an aqueous mixture at from 100° to 250° C. under autogenous pressure in the course of from 2 hours to 2 weeks during which the reaction mixture comprising a silicon, aluminum and phosphorus component is converted in aqueous organoamine solutions.

SAPO-5, for example, is obtained by mixing a suspension of $SiO_2$ in aqueous tetrapropylammonium hydroxide solution with an aqueous suspension of pseudoboehmite and orthophosphoric acid and subsequent reaction at from 150° to 200° C. under autogenous pressure in a stirred autoclave for from 20 to 200 hours. After the powder has been filtered off, it is dried at from 110° to 160° C. and calcined at from 450° to 550° C.

Suitable silicon aluminum phosphates are also ZYT-5, ZYT-6, ZYT-7, ZYT-9, ZYT-11 and ZYT-12.

Suitable phosphate catalysts for the process also include precipitated aluminum phosphates. Such an aluminum phosphate is prepared for example by dissolving 92 g of diammonium hydrogenphosphate in 700 ml of water. 260 g of $Al(NO_3)_3 \times H_2O$ in 700 ml of water are added dropwise in the course of 2 hours during which pH 8 is maintained by the simultaneous addition of 25% strength $NH_3$ solution. The resulting precipitate is subsequently stirred for 12 hours and then filtered off with suction and washed. It is dried at 60° C./17 h.

Suitable boron phosphates are preparable by mixing and kneading concentrated boric acid and phosphoric acid and by subsequent drying and calcination in inert gas, air or steam atmosphere at from 250° to 650° C., preferably at from 300° to 500° C.

These phosphates may have applied to them by impregnation (saturation and spraying) or in some cases even by ion exchange the hydrogenating components as described. As with the zeolite catalysts, a modification with a metal or an acid is also possible.

The catalysts can optionally be used in the form of from 2 to 4 mm extrudates or as tab-lets from 3 to 5 mm in diameter or as chips having particle sizes of from 0.1 to 0.5 mm, or in a fluidizable form.

The catalytic conversion is preferably carried out in the gas phase at from 100° to 500° C., preferably at from 200° to 400° C., at a weight hourly space velocity (WHSV) of from 0.1 to 20 $h^{-1}$, preferably of from 0.5 to 5 $h^{-1}$, of g of starting material per g of catalyst per hour.

The ratio of hydrogen:epoxy is advantageously 1–100 molar, in particular 3–30 molar.

The gas phase reaction can be carried out in a fixed bed or in a fluidized bed.

It is also possible to carry out the reaction in the liquid phase (by a suspension, trickle bed or liquid phase procedure) at from 50° to 200° C.

The process can be carried out under atmospheric pressure, under reduced pressure or under superatmospheric pressure, batchwise or preferably continuously.

Sparingly volatile or solid starting materials are used in dissolved form, for example in THF, toluene or petroleum ether solution. In general, the starting material may be diluted with such solvents or with inert gases such as $N_2$, Ar or $H_2O$ vapor.

After the reaction, the products formed are isolated from the reaction mixture in a conventional manner, for example by distillation; unconverted starting materials may be recycled into the reaction.

Preferably, the gaseous reaction products are immediately introduced into a separation stage and then split into their individual components. Such a separation can be carried out for example in a fractionating column.

EXAMPLES 1 TO 15

The reactions in the gas phase are carried out under isothermal conditions in a tubular reactor (coil, 0.6 cm in internal diameter, 90 cm in length) for at least 6 hours. The reaction products are separated off and characterized in a conventional manner. The quantitative determination of the reaction products and the starting materials is done by gas chromatography.

The catalysts used for the process according to the invention are:

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (mixture 50:50% by weight) at 170° C. under autogenous pressure in a stirred autoclave. After filtering and washing, the crystalline reaction product is dried at 100° C./24 h and calcined at 500° C./24 h. This borosilicate zeolite comprises 94.2% by weight of $SiO_2$ and 2.3% by weight of $B_2O_3$.

This material is molded with a molding aid into 2 mm extrudates which are dried at 110° C./16 h and calcined at 500° C./24 h.

Catalyst A is obtained by impregnating these extrudates with an aqueous $Cu(NO_3)_2$ solution, then drying at 130° C./2 h and calcining at 540° C./2 h. The Cu content is 3.4% by weight.

Catalyst B

Catalyst B is prepared in the same way as catalyst A, except that aqueous $Pd(NO_3)_2$ solution is used for the impregnation instead of $Cu(NO_3)_2$ solution. The Pd content is 0.5% by weight.

Catalyst C

The extrudates of the borosilicate zeolite described in connection with catalyst A are introduced into a column and subjected to an ion exchange with an ammoniacal palladium nitrate solution at 50° C. Washing with water is followed by drying at 110° C. and calcination at 500° C./5 h. The Pd content is 0.95% by weight.

Catalyst D

Catalyst D is prepared in the same way as catalyst A, except that an aqueous solution of Pd nitrate and Ce nitrate is used instead of Cu nitrate. The Pd content is 0.5% by weight and the Ce content 2.3% by weight.

Catalyst E

Catalyst E is obtained by impregnating catalyst C with ammonium sulfide solution. The S content is 0.35%.

Catalyst F

An aluminosilicate zeolite of the pentasil type is prepared under hydrothermal conditions and autogenous pressure at 150° C. from 65 g of finely divided $SiO_2$, 20.3 g of $Al_2(SO_4)_3 \times 18\ H_2O$ in 1 kg of an aqueous 1,6-hexane-diamine solution (mixture 50:50% by weight) in a stirred autoclave. After filtering and washing, the crystalline reaction product is dried at 110° C./24 h and calcined at 500° C./24 h. This aluminosilicate zeolite contains 91.6% by weight of $SiO_2$ and 4.6% by weight of $Al_2O_3$.

The catalyst is molded with a molding aid into 2 mm extrudates, dried at 110° C./16 h and calcined at 500° C./24h.

Catalyst F is obtained by impregnating these extrudates with an aqueous Cu(NO₃)₂ solution, then drying at 130° C./2 h and calcining at 540° C./2 h. The Cu content is 3.0% by weight.

Catalyst G

Silicon aluminum phosphate-5 (SAPO-5) is prepared from a mixture of 200 g of 98% strength phosphoric acid, 136 g of boehmite, 60 g of silica sol (30% strength), 287 g of tripropylamine and 587 g of H₂O. This mixture is reacted at 150° C. under autogenous pressure for 168 hours. After filtration, the crystalline product is dried at 120° C. and calcined at 500° C. SAPO-5 contains 49.8% by weight of $P_2O_5$, 33.0% by weight of $Al_2O_3$, and 6.2% by weight of $SiO_2$. SAPO-5 is molded together with an extrusion aid into 3 mm extrudates, dried at 120° C. and calcined at 500° C.

These extrudates are impregnated with an ammoniacal palladium nitrate solution. Washing with H₂O is followed by drying at 110° C. and calcination at 500° C./5 h. The Pd content is 1% by weight.

The experimental results obtained with these catalysts and the experimental conditions are summarized in the Table.

EXAMPLE 16

200 ml/h of styrene oxide are evaporated in a 400 l/h stream of hydrogen and passed at 260° C. over 1 l of catalyst A packed into a reaction tube electrically heated from the outside. The gaseous reaction products are condensed and worked up and characterized in a conventional manner. The phenylethanol is purified by conventional distillation. The distillation yield of phenylethanol is 78.4%.

TABLE 1

Preparation of phenylethanol (I) from styrene oxide (II)

| | Example | | | | | | | | |
|---|---|---|---|---|---|---|---|---|---|
| | 1 | 2 | 3 | 4 | 5 | 6 | 7 | 8 | 9 |
| Catalyst | A | A | A | B | C | D | E | F | G |
| Temperature (°C.) [°C.] | 300 | 300 | 250 | 250 | 250 | 250 | 250 | 250 | 300 |
| WHSV [h⁻¹]⁽¹⁾ | 3.0 | 2.5 | 1.5 | 1.5 | 2.5 | 2.5 | 1.5 | 1.5 | 1.5 |
| l of H₂/h | 3 | 7 | 15 | 7 | 7 | 7 | 7 | 15 | 7 |
| Conversion of (II) (%) | 100 | 100 | 100 | 100 | 100 | 100 | 100 | 100 | 100 |
| Selectivity of (I) [%] | 34.2 | 52.2 | 84.7 | 72.7 | 75.2 | 80.4 | 83.9 | 82.4 | 70.3 |
| Selectivity of (III)⁽²⁾ [%] | 49.3 | 22.9 | — | — | — | — | — | — | — |

⁽¹⁾based on feed of styrene oxide (II)
⁽²⁾phenylacetaldehyde (III)
⁽³⁾by-products are for example styrene, ethylbenzene, toluene and xylene.

TABLE 2

Preparation of substituted phenylethanols (I) from corresponding styrene oxides (II)

| | Example | | | | | |
|---|---|---|---|---|---|---|
| | 10 | 11 | 12 | 13 | 14 | 15 |
| Starting material | 4-Methyl- | 4-fluoro | 4-trifluoromethyl- | 4-Methoxy- | 2-Methyl-4-fluoro | 2-Methyl- |
| Catalyst | A | A | A | A | A | A |
| Temperature (°) | 250 | 250 | 250 | 250 | 250 | 250 |
| WHSV [h⁻¹] | 1.5 | 1.5 | 1.5 | 1.5 | 1.5 | 1.5 |
| l of H₂/h | 15 | 15 | 15 | 15 | 15 | 15 |
| Conversion of (I) (%) | 100 | 100 | 100 | 100 | 100 | 100 |
| Selectivity of (II) (%) | 90.2 | 81.5 | 85.2 | 87.4 | 75.3 | 88.7 |

WHSV is based on feed of styrene oxide.

We claim:

1. A process for preparing a phenylethanol of the formula (I)

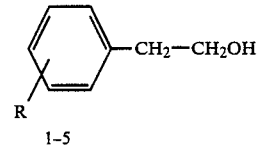

(I)

where R is hydrogen, alkyl of from 1 to 4 carbon atoms, alkoxy of from 1 to 4 carbon atoms-, fluorine, trifluoromethyl or trifluoromethoxy, which consisting essentially of reacting an epoxy of formula (II)

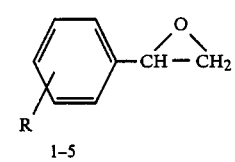

(II)

where R is as defined above, in the gas phase at from 100° to 500° in the presence of hydrogen over a zeolite or phosphate doped with a hydrogenating metal as a catalyst.

2. A process as claimed in claim 1, wherein the zeolite used is of the pentasil type.

3. A process as claimed in claim 1, wherein an aluminosilicate, borosilicate or iron silicate zeolite of the pentasil type is used.

4. A process as claimed in claim 1, wherein the zeolite used is of the faujasite, mordenite, erionite, chabazite or L-type.

5. A process as claimed in claim 1, wherein a phosphate of the elements Al, B, Fe, Zr or Ce is used.

6. A process as claimed in claim 1, wherein a hydrothermally prepared phosphate is used.

7. A process as claimed in claim 1, wherein a silicon aluminum phosphate, silicon boron phosphate, iron silicon aluminum phosphate, silicon iron phosphate, cobalt aluminum phosphate or cobalt silicon aluminum phosphate is used.

8. A process as claimed in claim 1, wherein the hydrogenating metal used is a metal of the Pt group, Ag, Ni, Co, Cu, Zn or a mixture thereof.

* * * * *